United States Patent
Langheinrich et al.

(10) Patent No.: US 8,009,793 B2
(45) Date of Patent: Aug. 30, 2011

(54) METHOD FOR IMAGING PLAQUE USING DUAL ENERGY CT

(75) Inventors: Alexander C. Langheinrich, Giessen (DE); Erik L. Ritman, Wabasha, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 325 days.

(21) Appl. No.: 12/280,192

(22) PCT Filed: Feb. 20, 2007

(86) PCT No.: PCT/US2007/004376
§ 371 (c)(1),
(2), (4) Date: Aug. 21, 2008

(87) PCT Pub. No.: WO2007/100550
PCT Pub. Date: Sep. 7, 2007

(65) Prior Publication Data
US 2010/0316274 A1 Dec. 16, 2010

Related U.S. Application Data

(60) Provisional application No. 60/776,645, filed on Feb. 24, 2006.

(51) Int. Cl.
*A61B 6/00* (2006.01)
(52) U.S. Cl. ....... 378/5; 378/98.11; 378/98.12; 382/130
(58) Field of Classification Search .................. 378/4, 5, 378/98.11, 98.12
See application file for complete search history.

(56) References Cited

U.S. PATENT DOCUMENTS

| | | | | | |
|---|---|---|---|---|---|
| 3,974,386 | A | * | 8/1976 | Mistretta et al. | 378/98.11 |
| 4,482,918 | A | * | 11/1984 | Keyes et al. | 378/98.11 |
| 4,541,106 | A | * | 9/1985 | Belanger et al. | 378/98.11 |
| 4,603,428 | A | | 7/1986 | Sandrik et al. | |
| 4,837,686 | A | | 6/1989 | Sones et al. | |
| 6,819,738 | B2 | | 11/2004 | Hoffman | |
| 6,836,528 | B2 | | 12/2004 | Reddy et al. | |
| 6,922,462 | B2 | | 7/2005 | Acharya et al. | |
| 7,031,426 | B2 | | 4/2006 | Iatrou et al. | |
| 2004/0101086 | A1 | * | 5/2004 | Sabol et al. | 378/4 |
| 2004/0101089 | A1 | * | 5/2004 | Karau et al. | 378/4 |
| 2004/0136491 | A1 | * | 7/2004 | Iatrou et al. | 378/4 |
| 2005/0180541 | A1 | * | 8/2005 | Avinash et al. | 378/5 |
| 2006/0159220 | A1 | * | 7/2006 | Heuscher | 378/9 |

OTHER PUBLICATIONS

Flohr et al., First performance evaluation of dual-source CT (DSCT) system, computer tomography, Eur Radiol, 16, 2006, pp. 256-268.*
Riederer et al., Selective iodine imaging using K-edge energies in computerized x-ray tomography, Am Assoc Phys Med, vol. 4, No. 6, 1977, pp. 474-481.*
International Search Report and Written Opinion for PCT/US2007/004376 with a mailing date of Apr. 2, 2008.
Barton, et al., Hemochromatosis, Cambridge University Press, 2000, pp. 219-222.

* cited by examiner

*Primary Examiner* — Edward J Glick
*Assistant Examiner* — Alexander H Taningco
(74) *Attorney, Agent, or Firm* — Quarles & Brady, LLP

(57) ABSTRACT

Two x-ray CT images are acquired of arterial plaque using x-rays at two different energy levels. The reconstructed images are normalized by adjusting pixel brightness until pixels depicting a region containing calcium have substantially the same brightness. The normalized images are subtracted to produce an image that depicts iron in the arterial plaque.

5 Claims, 4 Drawing Sheets

METHOD FOR IMAGING PLAQUE USING DUAL ENERGY CT

CROSS-REFERENCE TO RELATED APPLICATIONS

This application claims the benefit of U.S. Provisional patent application Ser. No. 60/776,645 filed on Feb. 24, 2006 and entitled "Imaging Vulnerable Plaque Using Dual Energy CT".

STATEMENT REGARDING FEDERALLY SPONSORED RESEARCH

This invention was made with government support under Grant No. HL65342 and EB000305 awarded by the National Institute of Health. The United States Government has certain rights in this Invention.

BACKGROUND OF THE INVENTION

The present invention relates to computed tomography (CT) imaging apparatus; and more particularly, to the imaging of arterial plaque.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique although a number of other methods are also used. This process converts the attenuation measurements from a scan into integers called "CT numbers" or "Hounsfield units", which are used to control the brightness of a corresponding pixel on a display.

Atherosclerosis is characterized by the formation of plaque in the patient's arteries. This plaque is asymptomatic until it blocks a substantial percentage of the artery or it ruptures and spawns a clot which flows down stream to block a smaller vessel. Many methods are available to detect the presence of plaque, but the ability to detect plaque that is vulnerable to becoming symptomatic is limited. The ultimate test of any hypothesis about plaque vulnerability and plaque rupture will depend on technologies that allow us to serially image advanced atherosclerotic lesions by non-invasive studies. Recently, MRI has been used to detect intraplaque hemorrhage in human carotid arteries. Basic requirements for clinically feasible imaging methods which detect enhanced vascularization by virtue of the enhanced perfusion of the lesion reflected by the increase in transient opacification of the arterial wall during an intravascular injection of contrast agent is high temporal and spatial resolution.

Contrast-enhanced multi-detector computed tomography (MDCT) permits reliable visualization of coronary arteries. Recent studies showed a high sensitivity and specifity of 16-slice MDCT for the detection of hemodynamically significant coronary stenosis and in addition to the luminal narrowing it is recognized that MDCT also visualizes the atherosclerotic diseased vessel wall directly. Calcified atherosclerotic lesions have been investigated extensively during the past years, indicating an association of calcified plaques and cardiovascular events. But up to now, imaging of non-calcified, advanced ("vulnerable") lesions remains elusive.

Intraplaque hemorrhage is an important process in the progression of asymptomatic plaques into high-risk unstable lesions, and neoangiogenesis of Vasa Vasorum (VV) is closely associated with lesion progression and is likely the primary source of intraplaque hemorrhage. In the past decade, rival techniques for assessment of atherosclerotic lesions have been developed, e.g. clinically: magnetic resonance imaging and multi-slice computed tomography or experimentally: serial section histology and micro-computed tomography. The relation of fibro-calcified lesions, as determined by CT using the Agatston score, and cardio-vascular events has been demonstrated in the past, but imaging of advanced, vulnerable lesions with clinical imaging modalities like CT or MRI has remained difficult if not impossible.

SUMMARY OF THE INVENTION

The present invention is a method for imaging vascular plaque to detect the presence of iron deposits that are indicative of vulnerable plaque. More specifically, two CT images are acquired at two different x-ray beam energy levels, the images are normalized such that calcium has substantially the same gray scale level in both images, and the two normalized images are subtracted to produce an image of the vasculature in which iron deposits can be seen if they are present in the plaque.

The present invention is based on the discovery that a change in CT number shows a linear relationship between iron and calcium concentrations at different energies. FIG. 3 is a log/log plot of the CT value at the different energies. The calcium and iron relations to their concentrations are linear but differ in off-set (gain in linear space). The subtraction of images obtained at different energies, such that the calcium signal cancels out ($\Delta_{Ca}=0$), will leave the iron signal as indicated in the smaller plot ($\Delta_{Fe}=I_{18}-1.534*I_{24}$). Images acquired at two energy levels were subtracted after the high-energy images were biased such that bone had the same gray scale as the lower-energy images. Areas identified as calcified lesions cancelled out, whereas those bright spots identified as iron deposits remain in the subtracted image. The development of calcified lesions and iron deposits within advanced atherosclerotic lesions is confirmed by histology. Iron and calcium deposits also accumulate in advanced lesions with high spatial coincidence and nearly similar size. The presence of iron in hemorrhaged lesions (AHA classification Type VIb) and calcium (AHA classification Type Vb) was confirmed by histology with high spatial correspondence.

DETAILED DESCRIPTION OF THE PREFERRED EMBODIMENT

Figure 1:
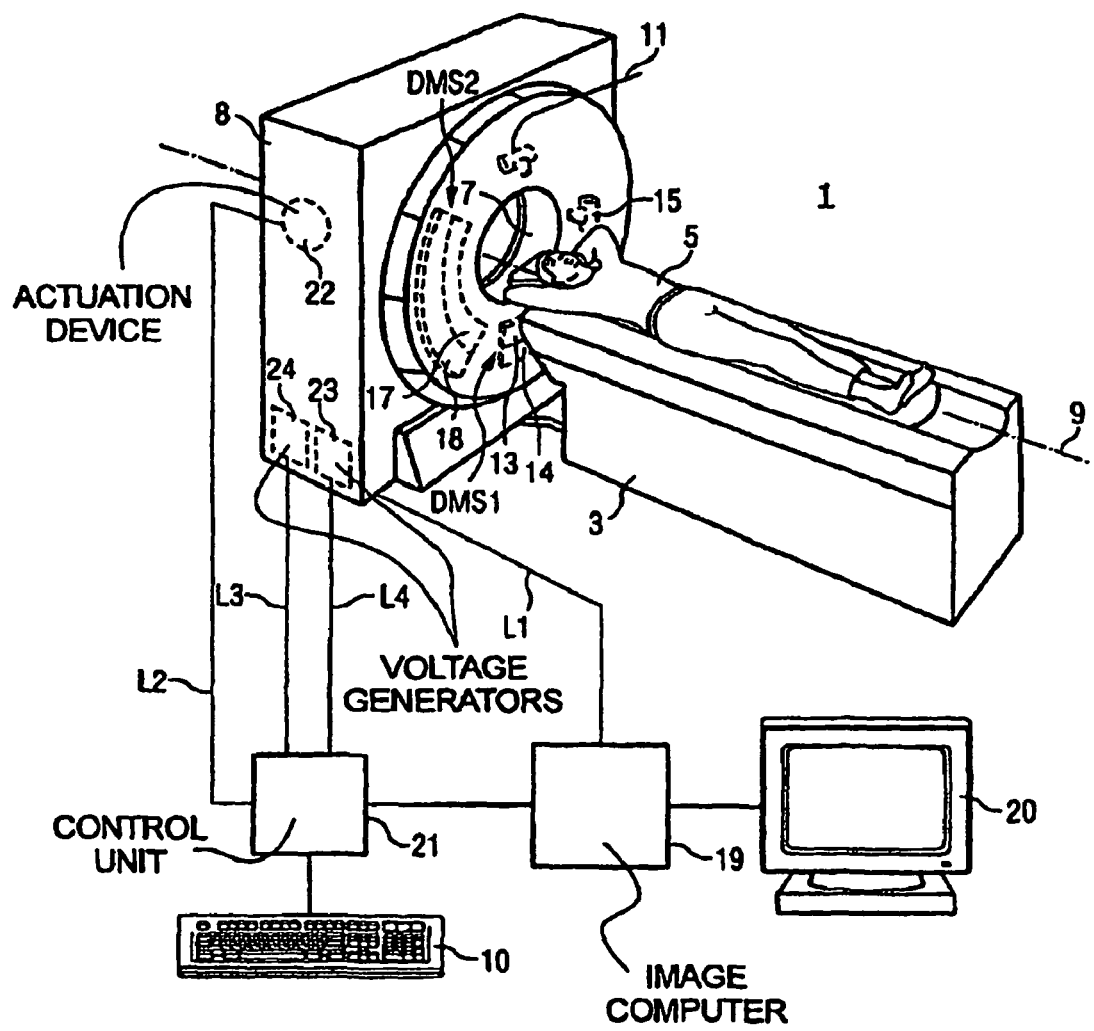
FIG. 1 is a pictorial view of a CT imaging system in which the present invention may be employed.

Referring to FIG. 1, the CT scanner 1 includes a patient table 3 for supporting and positioning an examination subject 5. The region of interest in the patient 5 can be inserted into an opening 7 (diameter 70 cm) in the housing 8 of the tomography apparatus 1 by means of a movable table top. Inside the housing 8, a gantry (not visible) is mounted so as to be rotated with high speed around a rotation axis 9 running through the patient. Moreover, for a spiral, or helical, scan a continuous axial feed is effected with the positioning device 3. A control unit 10 is provided for operation of the tomography apparatus 1 by a doctor or an assistant.

Two data acquisition systems are mounted on the gantry. A first acquisition system has an x-ray tube as a first radiator 11 and a first data acquisition unit DMS1 formed as a multi row x-ray detector array as a first detector 13. A second acquisition system has a separate x-ray tube as a second radiator 15 and furthermore a second data acquisition unit DMS2 formed as a separate multi row x-ray detector array as a second detector 17. The arrangement of the two radiators 11, 15 and the two detectors 13, 17 on the gantry is fixed during the operation of the tomography apparatus 1, such that their relative separations are constant during operation.

The x-ray detector arrays are fashioned on a base of an electronically readable scintillator ceramic, known as a UFC ceramic. Surface detectors, for example with 256 or more lines, alternatively can be used. The electronic signals generated by the x-ray detector arrays are conditioned in respective downstream electronic data processing units 14 and 18 that, together with the respective associated detector 13 and 17, form the data acquisition units DMS1 and DMS2. In the data processing units 14 and 18, the electronic signals are integrated and digitized.

The projection data of both acquisition systems are supplied via wiper rings or an optical transmission system to the stationary part of the gantry, and then to an image computer 19. In the image computer 19, the acquired projection views are processed using an image reconstruction method into a CT image that can be displayed on a display device 20. The image computer 19 is fashioned such that the reconstruction of an image can be implemented separately using projection data or raw data from each acquisition systems. As will be described in more detail below, these separate images are then processed to produce a single image which depicts iron deposits in the patient.

The tomography apparatus 1 is controlled by a control unit 21 that is connected with the image computer 19 and with the operating unit 10. The control unit is also connected with the data processing units 14 and 18 via a data transmission line L1. Moreover, the control unit 21 operates through lines L3, L4 two voltage generators 23, 24 that respectively supply the x-ray tubes 11 and 15 with energy.

Figure 2:
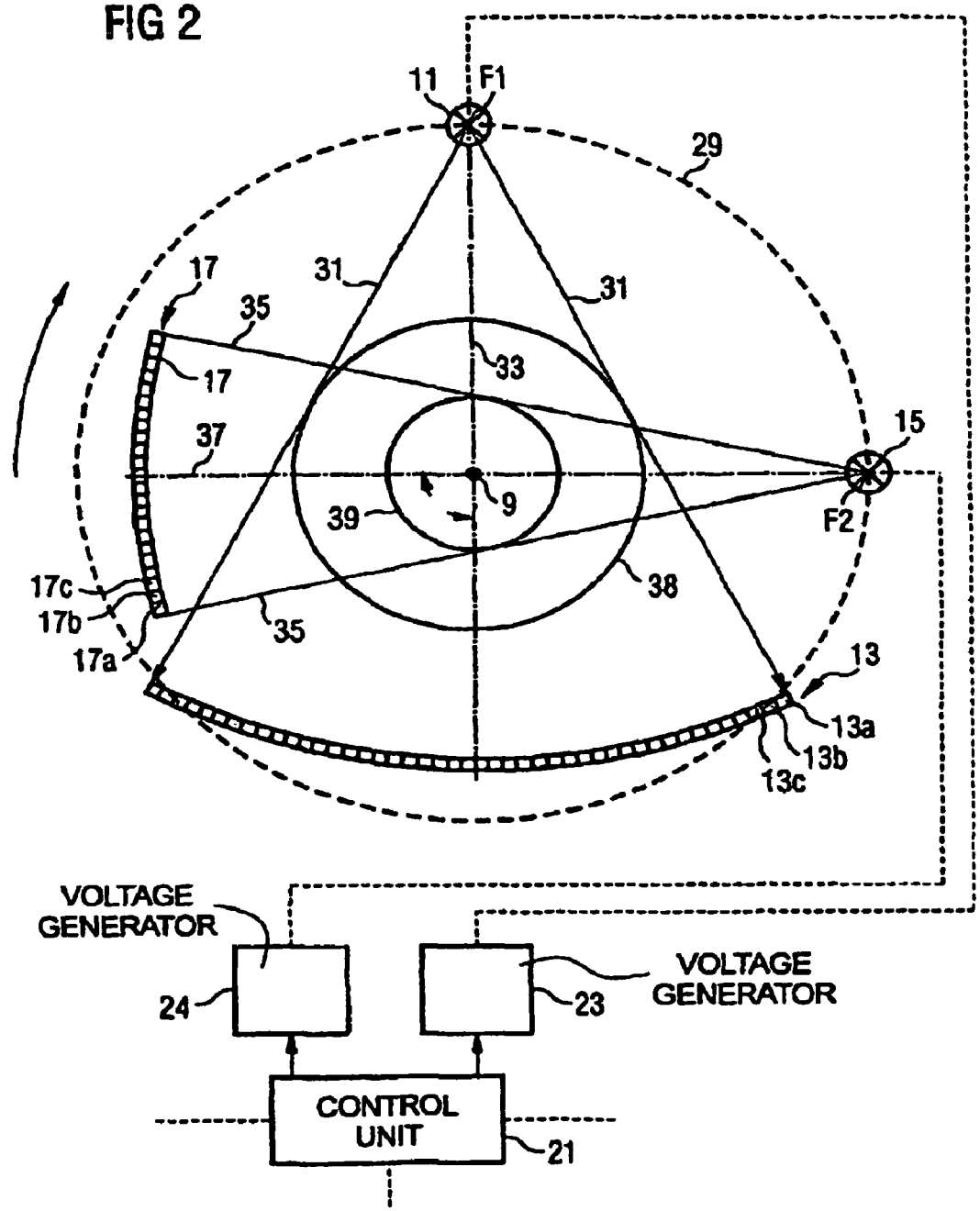
FIG. 2 is a block schematic diagram of the CT imaging system.
Figure 3:
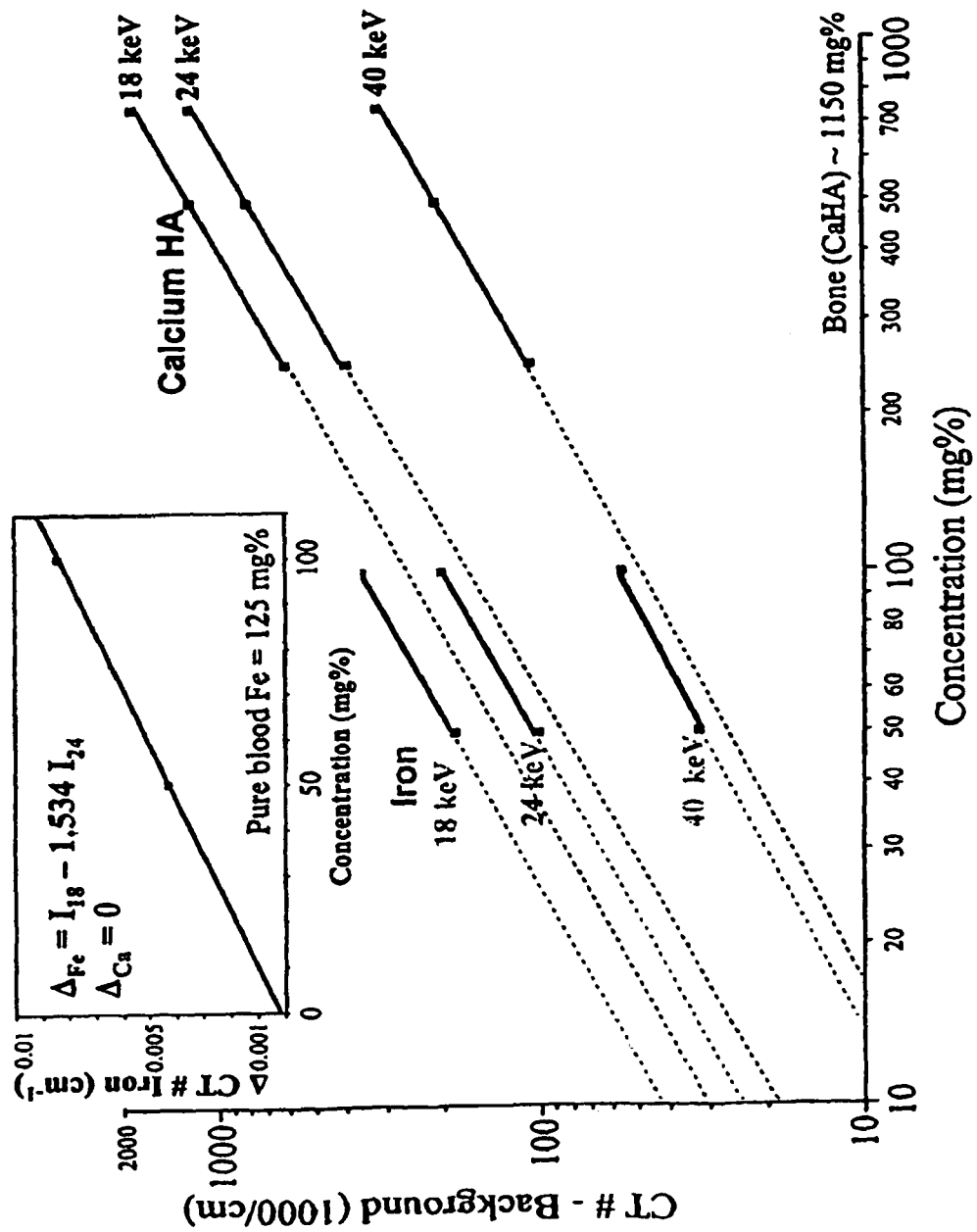
FIG. 3 is a graphic indication of the CT numbers of iron and calcium at different concentrations and x-ray beam energy levels.

FIG. 2 shows both acquisition systems of FIG. 1 in detail. In particular, both x-ray tubes 11, 15 (and the focus F1 and focus F2) rotate in the arrow direction on a common rotation path 29 around the rotation z-axis 9 (which is perpendicular to the plane of the drawing) and alternately radiate x-ray fan beams that are respectively shown with edge rays 31 and 35 and a middle rays 33 and 37. During the respective radiation, raw data are generated from different projection angles for a subsequent image reconstruction. In the cross-section of FIG. 2, only one line of the respective detectors 13 and 17 (with detector elements 13a, 13a, 13c and 17a, 17a, 17c, . . . ) is shown:

The length of each detector 13 and 17 is curved around the respective focus of the associated radiators 11 and 15, and are different, such that, in the representation of FIG. 2, detectable x-ray beams of different sizes arise for the two acquisition systems, and maximum measurement fields 38 and 29 of different sizes result.

The control unit 21 acts on the voltage generators 23, 24 such that the x-rays tubes or radiators 11, 15 alternately radiate. More importantly, the control unit 21 separately controls the voltage applied to each x-ray tube 11 and 15 such that two images may be acquired simultaneously from a region of interest in the patient at two different energy levels.

Figure 4:
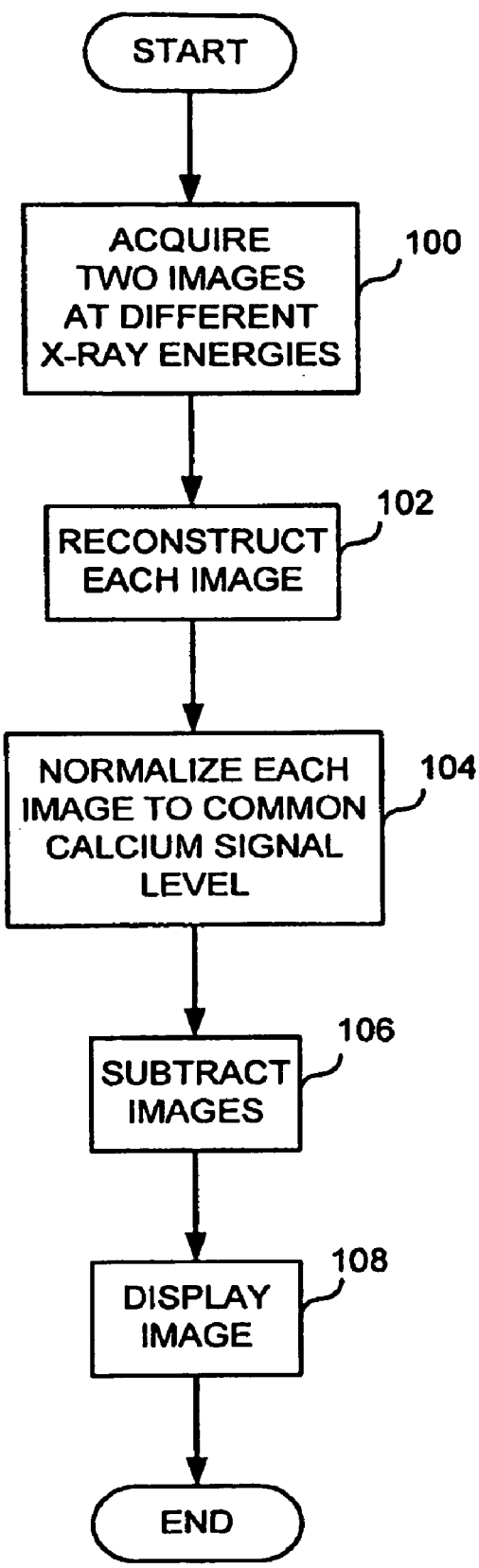
FIG. 4 is a flow chart of the preferred method for practicing the present invention.

Referring particularly to FIG. 4, the CT system is operated to simultaneously acquired two images from a region of interest in the patient at two different energy levels as indicated at process block 100. In the preferred embodiment energies of 80 and 120 kVp at 250 mAs were used. Each image is separately reconstructed as indicated at process block 102 using a conventional image reconstruction method.

As indicated at process block 104, the next step is to normalize the images such that the CT numbers for calcium are the same in both images. This is accomplished by identifying a region common to both images such as bone and adjusting the intensity level in one or both images until the pixels in this region have the same intensity. All of the image pixels are changed in this normalization step, and it is the change in pixels depicting iron that becomes different in the two images. The normalization can be done manually, but preferably it is performed automatically after the calcium region is selected.

As indicated at process block 106, the next step is to subtract one normalized image from the other. This is a subtraction of the CT numbers in one image from the CT numbers of the corresponding pixels in the other image. The resulting difference image depicts pixels containing iron deposits in arterial plaque at a brighter level. This image may be displayed as indicated at process block 108 along with diagnostic data such as the percentage of iron in a selected region of interest or the like.

It should be apparent that the simultaneous acquisition of both images as described above is preferred because the tissues depicted in the two images are perfectly aligned, or registered. This is required for the subtraction step to properly reveal iron. However, in the alternative the two images can be acquired sequentially and measures taken to limit patient motion, or to correct for patient motion. For example, a single x-ray generator may be employed at one energy level to acquire one image and then the same x-ray generator may be employed at a second energy level to acquire a second image.

Based on our findings, iron deposits can be identified and quantitated, and plaque hemorrhage in human coronary arteries can be identified with clinical CT scanners using dual energy CT imaging. Consequently, the combined imaging of transient plaque opacification (as an index of vasa vasorum density) and plaque iron deposits, form a basis for CT imaging-based identification of vulnerable plaques.

What is claimed is:

1. A method for imaging iron in arterial plaque with an x-ray computed tomography (CT) system, the steps comprising:
   a) acquiring image data of the plaque using the CT system operating at a first x-ray energy level;
   b) acquiring image data of the plaque using the CT system operating at a second x-ray energy level;
   c) reconstructing two images from the data acquired in respective steps a) and b);
   d) normalizing the reconstructed images by adjusting the levels of pixel intensities such that pixels depicting calcium have substantially the same intensity; and
   e) producing an image depicting iron by subtracting the normalized images produced in step d).

2. The method as recited in claim 1 in which steps a) and b) are performed substantially simultaneously by using two x-ray tubes and detector arrays in the CT system.

3. The method as recited in claim 1 in which step d) includes:
   d)i) selecting a region common to both images which contains calcium; and
   d)ii) adjusting the pixel levels in one image until the brightness of pixels in the selected region is substantially the same in both images.

4. The method as recited in claim 1, wherein the normalizing the reconstructed images includes using a change in a CT number that represents a linear relationship between iron and calcium concentration at different x-ray energies.

5. The method as recited in claim 1, wherein the producing an image depicting iron includes producing an image representing non-calcified arterial plaque.

* * * * *